United States Patent
Willett et al.

(10) Patent No.: US 10,823,717 B2
(45) Date of Patent: Nov. 3, 2020

(54) WIRELESS POWER TRANSFER AND SENSING FOR MONITORING PIPELINES

(71) Applicant: 3M INNOVATIVE PROPERTIES COMPANY, St. Paul, MN (US)

(72) Inventors: Stephen J. Willett, St. Paul, MN (US); Ronald D. Jesme, Plymouth, MN (US); Mohsen Salehi, Woodbury, MN (US); Andrew P. Bonifas, Edmonton (CA); Erik A. Aho, New Richmond, WI (US); Craig R. Schardt, Woodbury, MN (US); Amy J. Hite, Cottage Grove, MN (US); Patrick M. Campbell, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 456 days.

(21) Appl. No.: 15/693,725

(22) Filed: Sep. 1, 2017

(65) Prior Publication Data

US 2019/0072532 A1 Mar. 7, 2019

(51) Int. Cl.
*H02J 50/20* (2016.01)
*G01N 33/00* (2006.01)
(Continued)

(52) U.S. Cl.
CPC .......... *G01N 33/0062* (2013.01); *G01M 3/18* (2013.01); *G01M 3/22* (2013.01); *G01N 33/0011* (2013.01);
(Continued)

(58) Field of Classification Search
CPC .......... G01N 33/0062; G01N 33/0011; G01N 33/225; G01M 3/22; G01M 3/18; H02J 50/001; H02J 50/20
See application file for complete search history.

(56) References Cited

U.S. PATENT DOCUMENTS

| 4,289,019 A | 9/1981 | Claytor |
| 7,109,716 B2 | 9/2006 | Takach |
(Continued)

FOREIGN PATENT DOCUMENTS

| CN | 202837291 | 3/2013 | |
| WO | WO-03030300 A1 * | 4/2003 | ......... G06K 19/0726 |
| WO | WO 2010/006091 | 1/2010 | |

OTHER PUBLICATIONS

3M Dynatel, Electronic Marking System (EMS), Marker Locator with iD Read/Write 7420, Operator's Manual, 3M Company (Jul. 2015), 30 pgs.

(Continued)

*Primary Examiner* — Daniel J Cavallari

(57) ABSTRACT

A system for use in wirelessly monitoring a pipeline such as a natural gas pipe. The system includes a locator configured to wirelessly transmit power and a subsoil sensor marker located adjacent the pipe and configured to wirelessly communicate with the locator. The sensor marker includes a microcontroller, a memory module, a sensor configured to sense the presence of a gas, and a power module. The power module is configured to harvest a sufficient amount of the power wirelessly transmitted from the locator in order to operate the microcontroller to take a measurement via the sensor, save the measurement in the memory module, and wirelessly transmit the measurement to the locator.

19 Claims, 2 Drawing Sheets

(51) Int. Cl.
 G01M 3/22 (2006.01)
 G01M 3/18 (2006.01)
 G01N 33/22 (2006.01)
 H02J 50/00 (2016.01)
(52) U.S. Cl.
 CPC .......... G01N 33/225 (2013.01); H02J 50/001 (2020.01); H02J 50/20 (2016.02)

(56) References Cited

U.S. PATENT DOCUMENTS

| | | | |
|---|---|---|---|
| 7,616,119 B2* | 11/2009 | Corbett, Jr. | G01V 15/00 340/572.1 |
| 7,786,867 B2 | 8/2010 | Hamel et al. | |
| 2005/0251343 A1 | 11/2005 | Zehavi | |
| 2006/0136007 A1* | 6/2006 | Mickle | A61N 1/36067 607/45 |
| 2007/0210929 A1 | 9/2007 | Sabata et al. | |
| 2008/0079396 A1* | 4/2008 | Yamazaki | H02J 7/025 320/128 |
| 2011/0248857 A1 | 10/2011 | Rutherford et al. | |
| 2012/0155133 A1 | 6/2012 | Kim et al. | |
| 2013/0099790 A1 | 4/2013 | Doany et al. | |
| 2013/0200165 A1* | 8/2013 | Downie | G06K 19/0709 235/492 |
| 2013/0278412 A1 | 10/2013 | Kelly et al. | |
| 2015/0185134 A1* | 7/2015 | Chen | G01N 17/02 340/539.1 |
| 2016/0356665 A1 | 12/2016 | Felemban et al. | |
| 2017/0026722 A1* | 1/2017 | Schwartz | H04W 4/70 |
| 2019/0328230 A1* | 10/2019 | Schumacher | A61B 5/686 |

OTHER PUBLICATIONS

PCT International Search Report for International Application No. PCT/IB2018/056352, dated Dec. 17, 2018 (4 pages).

* cited by examiner

WIRELESS POWER TRANSFER AND SENSING FOR MONITORING PIPELINES

BACKGROUND

With an aging energy infrastructure in the US, especially the natural gas distribution infrastructure, the occurrence and danger associated with leaking natural gas pipelines is a growing trend. Pinpointing leaks in natural gas pipelines is a process to spatially identify the location of the pipeline leak. The identification and general location of a gas leak is known prior to the pinpointing process. Efficient leak pinpointing methods are critical to utilities companies to minimize overall distribution costs. The art of leak pinpointing is typically an expensive, time consuming, and inaccurate science. The pinpointing process usually involves locating the buried pipeline, drilling "bar holes" along the pipeline, and using a methane sensing device to detect the concentration of methane in the bar holes. The bar hole with the highest methane concentration is used to locate the gas leak. After a successful leak repair, the bar holes are filled and repaved at an additional cost. Accordingly, a need exists for an improved system and method for leak detection and pinpointing.

SUMMARY

A sensor marker for use in monitoring a pipeline, consistent with the present invention, includes a microcontroller, a memory module electrically coupled to the microcontroller, a sensor electrically coupled to the microcontroller and configured to sense the presence of a gas, and a power module. The power module is configured to wirelessly harvest power received from an antenna such that the harvested power is sufficient to operate the microcontroller to take a measurement via the sensor, save the measurement in the memory module, and wirelessly transmit the measurement.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Embodiments of this invention include a remotely powered methane sensor marker to monitor subsoil methane concentration to enable effective leak pinpointing of natural gas pipelines or other pipelines. The sensor marker is remotely powered by wirelessly harvesting power from a radio frequency (RF) radiation source and can wirelessly transmit measurement data collected from a low power subsoil sensor. The measurement data can include the presence of methane and possibly additional gasses and liquids. The sensor can also include a low power moisture sensor to sense soil desiccation caused by the presence of a methane leak.

The wireless powering and data communication features of the sensor marker provide for an advantage of eliminating the costly and time consuming need to drill destructive bar holes to take subsoil measurements. In particular, this invention includes the ability to remotely and wirelessly locate the presence of a buried gas sensor marker and then interrogate the sensor marker to determine the methane concentration at the location of the sensor marker. This interrogation process is expected to take on the order of 10 seconds to 10 minutes, although the actual interrogation time can dependent upon specific implementations of this invention. In some implementations, the majority of the interrogation time is associated with the wireless transfer and storage of energy needed to execute a sensing measurement. Another advantage of this invention includes low power electronics and methane sensing element that can enable battery-free operation with wireless communication of data.

Figure 1:
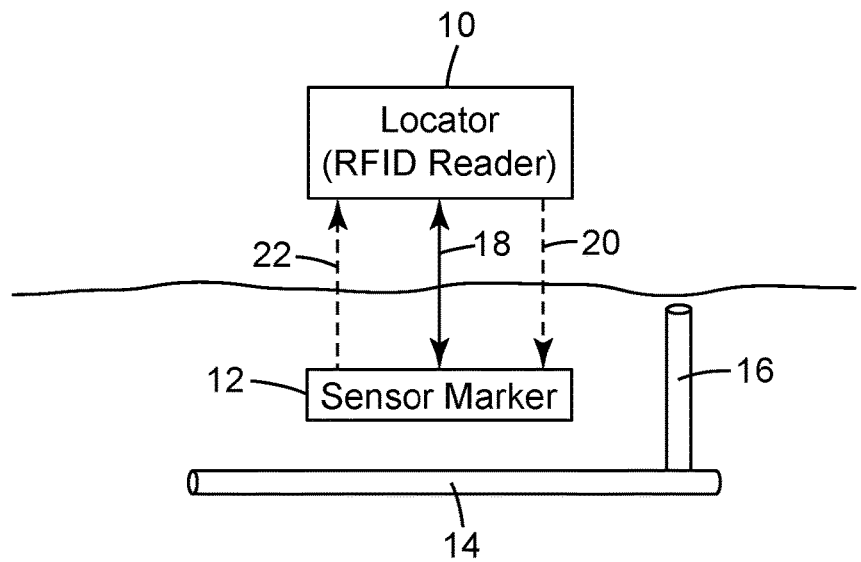
FIG. 1 is a diagram conceptually illustrating a wireless sensor system.

FIG. 1 is a diagram conceptually illustrating the wireless sensor system. A sensor marker 12 is located underground adjacent a pipeline to be monitored. The pipeline can include a main natural gas pipe 14 connected with a natural gas pipe 16 for delivering natural gas to a home or other building. A locator 10 is used to wirelessly detect and provide power (20) to sensor marker 12 which, in response, provides sensor data and communication (22) to locator 10. The system is designed such that when locator 10 is within a particular distance 18 from sensor marker 12, locator 10 can wirelessly transmit sufficient power to sensor marker 12 in order to operate the components of sensor marker 12. Multiple sensor markers would be placed underground at various locations adjacent a natural gas pipe in order to monitor the gas pipe and pinpoint leaks within it by using the locator to wirelessly read the sensor markers as those locations. The sensor marker, among those multiple sensor markers, providing the highest measurement reading of methane detection could be used to pinpoint a leak.

Figure 2:
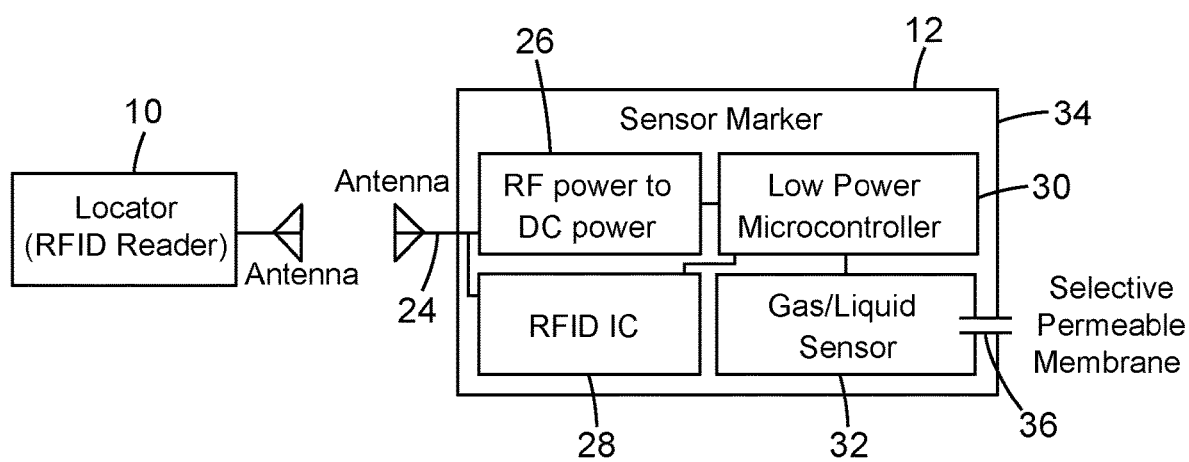
FIG. 2 is a block diagram of a locator and sensor marker for the system.

FIG. 2 is a block diagram of an exemplary locator 10 and an exemplary sensor marker 12 for the system. Locator 10 can be implemented with, for example, a radio frequency identification (RFID) reader with high power. Sensor marker 12 includes an RF power to direct current (DC) power module 26 for receiving and harvesting power from an antenna 24 and converting the harvested power to DC. Power module 26 is electrically coupled to an RFID integrated circuit (IC) module 28 and a lower power microcontroller or processor 30. Sensor marker 12 also includes a gas/liquid sensor 32 for taking a measurement via a selective permeable membrane 36 in a housing 34 containing the components of sensor marker 12. Gas/liquid sensor 32 can include only a gas sensor, or both a gas sensor and a moisture sensor. Housing 34 can be implemented with, for example, a sealed metal enclosure, aside from membrane 36, to provide environmental protection of the components of sensor marker 12 when located underground.

Microcontroller 30 is electrically coupled to gas/liquid sensor 32 and RFID IC module 28 in order to receive a measurement from gas/liquid sensor 32 and store the measurement in RFID IC module 28. In use, when locator 10 is close enough to sensor marker 12, within distance 18 between them, power module 26 can harvest a sufficient amount of RF power received via antenna 24 in order to operate RFID IC module 28, microcontroller 30, and gas/liquid sensor 32 via microcontroller 30.

Figure 3:
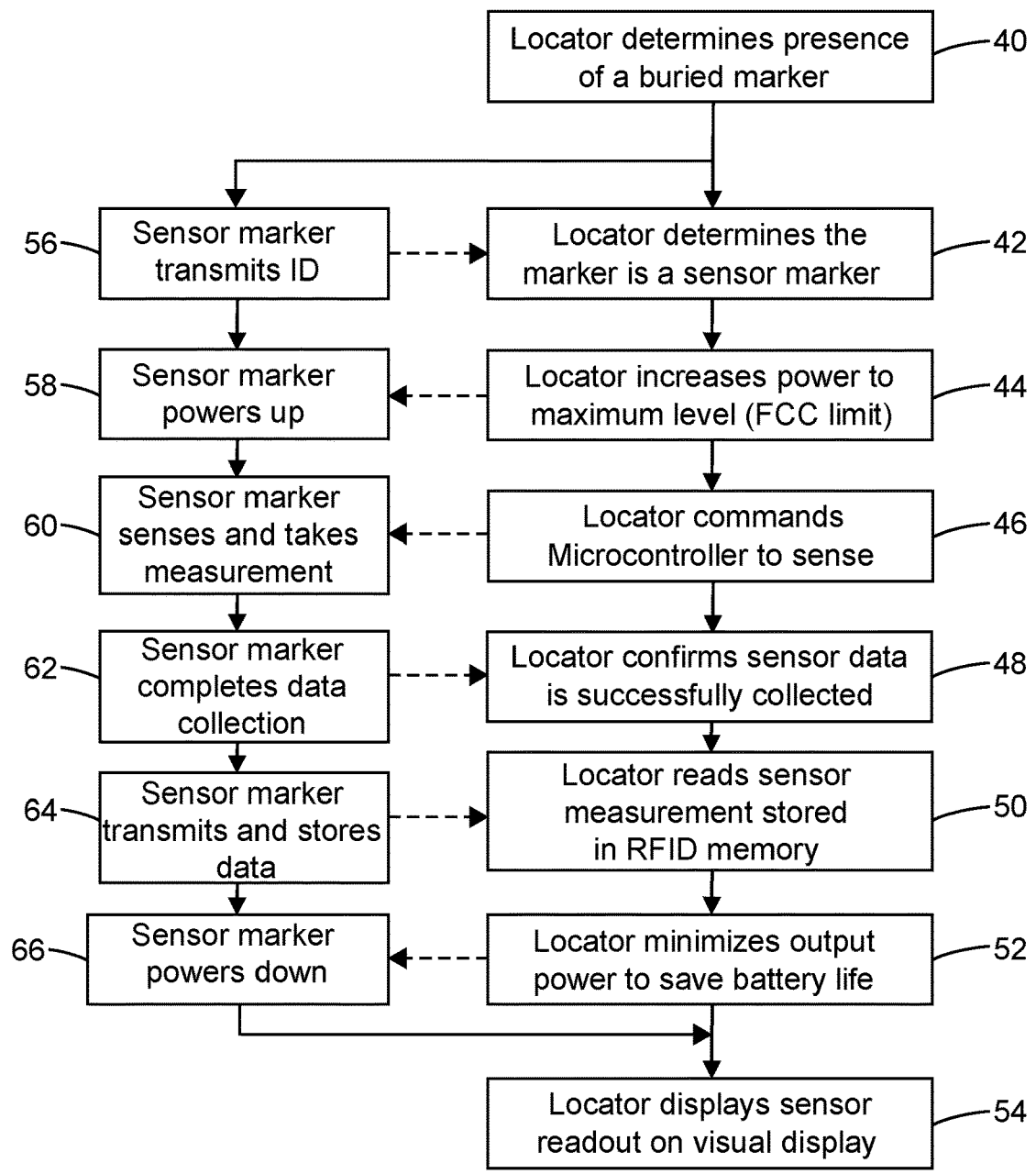
FIG. 3 is a flow chart of a method for operating the locator with a sensor marker.

FIG. 3 is a flow chart of a method for operating locator 10 with sensor marker 12. Locator 10 and microcontroller 30 can operate under software or firmware control to execute the steps of this method.

Locator 10 determines the presence of a marker buried underground by taking readings at particular locations (step 40). Locator 10 determines the detected marker is a sensor marker, such as sensor marker 12 (step 42), by receiving an identification (ID) of the detected marker when sensor marker 12 transmits its ID (step 56). In particular, the ID can encode or contain information indicating that this marker is a sensor marker having active capability to take a measurement, for example sense and report the condition of its immediate environment such as gas concentration or desiccation. The ID can also encode or contain other types of information such as the location and identity (e.g., lot number) of an adjacent underground asset, such as a pipeline, being monitored by the sensor marker.

Locator 10 increases the transmitted power to a maximum level (step 44) and, in response, sensor marker 12 powers up by power module 26 harvesting power received from antenna 24 (step 58). Step 58 can include the accumulation and storage of received power to ensure that adequate energy is available to execute a sensing measurement.

Locator 10 commands microcontroller 30 to sense (step 46) and, in response, sensor marker 12 senses and takes a measurement by using microcontroller 30 to receive a measurement from gas/liquid sensor 32 (step 60). Locator 10 confirms the sensor data is successfully collected (step 48) when sensor marker 12 completes the data collection of one or more measurements (step 62). Locator 10 reads the sensor measurement stored in the memory of RFID IC module 28 (step 50) when sensor marker 12 transmits the measurement data along with, for example, the date and time of measurement, and sensor marker 12 can also store the measurement data to track historical measurement readings (step 64). Other data stored and transmitted by the sensor marker can include a geographic location of the sensor marker to help pinpoint a location of leaks, for example the latitude and longitude coordinates of the sensor marker location or a street address closest to the sensor marker.

Locator 10 minimizes the transmitted output power to save battery life in sensor marker 12 (step 52), and sensor marker 12 powers down (step 66). Locator 10 can display the sensor measurement on a visual display or user interface on locator 10 and possibly also store the measurement in locator 10 (step 54).

The following are exemplary components for implementing the sensor system.

Locator 10 can be implemented with a high power RFID reader such as the Dynatel Locator 7420 product from 3M Company, or other types of readers capable of wirelessly powering and communicating with the sensor marker using, for example, air-core or ferrite windings antennas. An example of such an RF transmitting antenna is disclosed in US Patent Application Publication No. 2013/0099790, which is incorporated herein by reference as if fully set forth.

Microcontroller 30 can be implemented with the PIC12LFXX microcontroller from Microchip Technology Inc., or other types of microcontrollers or processors capable of operating under the power wirelessly harvested by the sensor marker.

Figure 4:
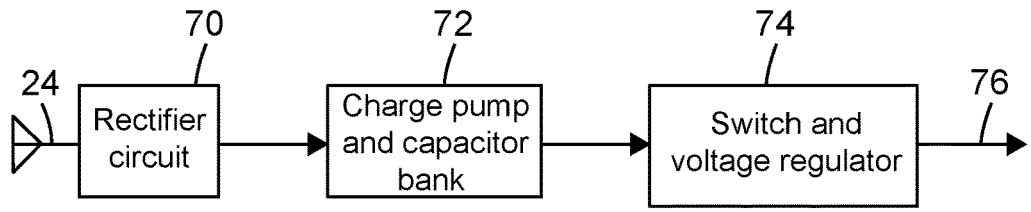
FIG. 4 is a block diagram of an RF power to DC power module.

RF power to DC power module 26 can be implemented with any circuit capable of harvesting sufficient power and converting it to DC for operating the components of the sensor marker. FIG. 4 is a block diagram of an exemplary circuit for implementing power module 26. This circuit includes a rectifier circuit 70 receiving RF power from antenna 24 and converting the RF power to DC power. A charge pump and capacitor bank 72, electrically coupled to rectifier 70, receives the DC power and stores charge in a capacitor bank such as a super capacitor. A switch and voltage regulator 74 (thyristor and voltage divider), electrically coupled to charge pump and capacitor bank 72, provides DC power on output 76 at a desired voltage and duration once sufficient energy is stored in the capacitor bank. In particular, when a predetermined voltage by the voltage divider is found at the thyristor, the stored energy is released, and the thyristor then remains conducting until all of the energy stored is released. The thyristor switch thus provides an advantage when used in the circuit of FIG. 4 in that the thyristor switches the voltage regulator on only when enough energy has been accumulated and allows all of the useful energy accumulated to be used by the load. Other types of circuits are possible for implementing switch and voltage regulator 74. Microcontroller 30 would be electrically coupled to output 76 to receive the DC power required for its operation. In other embodiments, the DC power from rectifier circuit 70 can be sufficient to power microcontroller 30 and gas/liquid sensor 32, in which case charge pump and capacitor bank 72 is not needed or need not be activated.

RFID IC module 28 can be implemented with any RFID IC or tag, or other types of memory modules, having sufficient memory to store sensor measurements and possibly other data such as date and time stamps.

Gas/liquid sensor 32 can be implemented with the Figaro TGS8410 methane sensor from Figaro USA Inc., or other gas sensors or gas and moisture sensors.

Antenna 24 for receiving the RF power from the locator can be implemented with, for example, an air-core winding with a large area, to maximize the flux received, but balanced against a desire for compact devices. Tables 1 and 2 provide parameters for exemplary antennas 1 and 2 to implement antenna 24 for wirelessly receiving power from the locator and wirelessly transmitting data to the locator. When tested, the power collected by antenna 1 from the Dynatel 7420 Locator at 5.5 ft was 2.3 µW, and the power collected by antenna 2 from the Dynatel 7420 Locator at 11 ft was 1.4 µW. Other designs for antenna 24 are possible depending upon, for example, the power requirements for the sensor marker and separation distance from the locator. Table 3 shows calculated power transferred from a Dynatel 7420 Locator to LC (inductor-capacitance) circuits with various radii and separation distances between the Dynatel 7420 Locator and the LC circuits, where $P(\mu W)=\alpha(\pi^2 a^4/d^6) \approx 2.3 \times 10^9 (\pi^2 a^4/d^6)$, 2a is the antenna diameter, d is the locator-antenna separation distance, and $\alpha$ is a fitting coefficient.

TABLE 1

| Antenna 1 | |
| --- | --- |
| Diameter | 3.6 in |
| Area | 10.2 in$^2$ |
| Wire Gauge | 18 Gauge Inductor Wire |
| Turns | 46 turns |
| Inductance | 160 µH |
| Capacitance | 21.5 nF |
| Resonant Frequency | 86 kHz |
| Quality Factor | 65 |

TABLE 2

Antenna 2

| | |
|---|---|
| Diameter | 8.5 in |
| Area | 56.75 in$^2$ |
| Wire Gauge | 18 Gauge Inductor Wire |
| Turns | 25 turns |
| Inductance | 278 µH |
| Capacitance | 13.2 nF |
| Resonant Frequency | 83 kHz |
| Quality Factor | 52 |

TABLE 3

| LC Diameter (in) | Separation Distance (in) | $\pi^2 a^4/d^6$ (in$^{-2}$) | Estimated Available Power (µW) |
|---|---|---|---|
| 4 | 24 | 8.26328E−07 | 1900.6 |
| 4 | 36 | 7.25445E−08 | 166.9 |
| 6 | 24 | 4.18328E−06 | 9621.6 |
| 6 | 36 | 3.67257E−07 | 844.7 |
| 8 | 24 | 1.32212E−05 | 30408.9 |
| 8 | 36 | 1.16071E−06 | 2669.6 |
| 8 | 48 | 2.06582E−07 | 475.1 |

The invention claimed is:

1. A sensor marker for use in monitoring a pipeline, comprising:
    a microcontroller;
    a memory module electrically coupled to the microcontroller;
    a sensor, electrically coupled to the microcontroller, configured to sense the presence of a gas; and
    a power module, electrically coupled to the microcontroller, configured to wirelessly harvest power received from an antenna,
    wherein the microcontroller is configured, via operating under the harvested power, to take a measurement via the sensor, save the measurement in the memory module, and wirelessly transmit the measurement,
    wherein the power module comprises a rectifier circuit electrically coupled to a switch and voltage regulator to convert the harvested power to direct current, and further comprises a charge pump and capacitor bank electrically coupled between the rectifier circuit and the switch and voltage regulator,
    wherein the voltage regulator is configured to turn on only when a particular amount of energy is stored in the capacitor bank.

2. The sensor marker of claim 1, wherein the microcontroller is configured, via operating under the harvested power, to transmit an identification of the sensor marker.

3. The sensor marker of claim 1, wherein the antenna comprises an air-core winding.

4. The sensor marker of claim 1, wherein the memory module comprises a radio frequency identification (RFID) module.

5. The sensor marker of claim 1, wherein the sensor comprises a methane sensor.

6. The sensor marker of claim 1, wherein the sensor is further configured to sense the presence of moisture.

7. The sensor marker of claim 1, further comprising a housing containing the microcontroller, the memory module, the sensor, and the power module, wherein the housing incudes a permeable membrane for the sensor to sense the presence of the gas.

8. A system for use in monitoring a pipeline, comprising:
    a locator configured to wirelessly transmit power; and
    a sensor marker, comprising:
        a microcontroller;
        a memory module electrically coupled to the microcontroller;
        a sensor, electrically coupled to the microcontroller, configured to sense the presence of a gas; and
        a power module, electrically coupled to the microcontroller, configured to harvest the power wirelessly transmitted from the locator and received from an antenna,
        wherein the microcontroller is configured, via operating under the harvested power, to take a measurement via the sensor, save the measurement in the memory module, and wirelessly transmit the measurement to the locator,
        wherein the power module comprises a rectifier circuit electrically coupled to a switch and voltage regulator to convert the harvested power to direct current, and further comprises a charge pump and capacitor bank electrically coupled between the rectifier circuit and the switch and voltage regulator,
        wherein the voltage regulator is configured to turn on only when a particular amount of energy is stored in the capacitor bank.

9. The system of claim 8, wherein the microcontroller is configured, via operating under the harvested power, to transmit an identification of the sensor marker.

10. The system of claim 8, wherein the antenna comprises an air-core winding.

11. The system of claim 8, wherein the memory module comprises a radio frequency identification (RFID) module.

12. The system of claim 8, wherein the sensor comprises a methane sensor.

13. The system of claim 8, wherein the sensor is further configured to sense the presence of moisture.

14. The system of claim 8, wherein the microcontroller is configured to:
    transmit an identification of the sensor marker;
    receive from the locator a command to sense;
    take the measurement via the sensor;
    save the measurement in the memory module; and
    wirelessly transmit the measurement to the locator.

15. The system of claim 8, wherein the locator is configured to:
    receive an identification from the sensor marker;
    command the sensor marker to sense; and
    read the measurement from the sensor marker.

16. The system of claim 8, wherein the locator comprises a radio frequency identification (RFID) reader.

17. The system of claim 8, further comprising a housing containing the microcontroller, the memory module, the sensor, and the power module, wherein the housing incudes a permeable membrane for the sensor to sense the presence of the gas.

18. The sensor marker of claim 2, wherein the identification further includes a location of an underground asset being monitored by the sensor marker.

19. The system of claim 9, wherein the identification further includes a location of an underground asset being monitored by the sensor marker.

* * * * *

UNITED STATES PATENT AND TRADEMARK OFFICE
CERTIFICATE OF CORRECTION

PATENT NO. : 10,823,717 B2
APPLICATION NO. : 15/693725
DATED : November 3, 2020
INVENTOR(S) : Stephen Willett Page 1 of 1

It is certified that error appears in the above-identified patent and that said Letters Patent is hereby corrected as shown below:

In the Claims

Column 5, Line 64 (approx.), in Claim 7, delete "incudes" and insert -- includes --, therefor.

Column 6, Line 55, in Claim 17, delete "incudes" and insert -- includes --, therefor.

Signed and Sealed this
Nineteenth Day of January, 2021

Andrei Iancu
*Director of the United States Patent and Trademark Office*